(12) United States Patent
Watkins et al.

(10) Patent No.: US 8,758,707 B2
(45) Date of Patent: Jun. 24, 2014

(54) STAINING INSTRUMENTS AND METHODS

(75) Inventors: Andrew Watkins, Fitzroy North (AU); Nathan Ray, Mitcham (AU); David Huang, Surrey Hills (AU)

(73) Assignee: Leica Biosystems Melbourne Pty Ltd, Mount Waverly (AU)

( * ) Notice: Subject to any disclaimer, the term of this patent is extended or adjusted under 35 U.S.C. 154(b) by 0 days.

(21) Appl. No.: 12/999,259

(22) PCT Filed: Jun. 16, 2009

(86) PCT No.: PCT/AU2009/000771
§ 371 (c)(1),
(2), (4) Date: Mar. 30, 2011

(87) PCT Pub. No.: WO2009/152569
PCT Pub. Date: Dec. 23, 2009

(65) Prior Publication Data
US 2011/0174088 A1 Jul. 21, 2011

Related U.S. Application Data

(60) Provisional application No. 60/061,767, filed on Jun. 16, 2008.

(30) Foreign Application Priority Data

Jun. 16, 2008 (AU) ................................ 2008903057

(51) Int. Cl.
*B01L 3/02* (2006.01)
*G01N 1/30* (2006.01)

(52) U.S. Cl.
USPC ........... 422/521; 422/509; 422/518; 422/539; 422/563; 422/63; 422/67; 422/68.1

(58) Field of Classification Search
USPC .......... 422/63–68.1, 501, 509, 536, 563, 518, 422/521; 436/46, 180; 73/863.32, 863.33, 73/864, 864.01, 864.11, 864.24, 864.25
See application file for complete search history.

(56) References Cited

U.S. PATENT DOCUMENTS 5,439,649 A * 8/1995 Tseung et al. ................. 422/510
7,303,725 B2 * 12/2007 Reinhardt et al. .............. 422/63
(Continued)

FOREIGN PATENT DOCUMENTS

| EP | 1 717 571 | 11/2006 |
|---|---|---|
| WO | WO 03/091710 | 11/2003 |
| WO | WO 2004/001390 | 12/2003 |

*Primary Examiner* — Brian R Gordon
(74) *Attorney, Agent, or Firm* — Sughrue Mion, PLLC

(57) ABSTRACT

An apparatus and method for applying reagents to tissue mounted on slides, in the field of histology is disclosed. The apparatus holds a number of slides, in slide trays, which are loaded onto the apparatus. Each slide tray forms a batch of slides, with all the batched forming a group. The apparatus holds a number of reagents, grouped into a first group comprising bulk type reagents, and a second group comprising antibodies or probes, and detection systems, for identifying elements of the tissue. A group fluid dispenser, in the form of a robot arm, dispense reagents to the group of slides. Each batch of slides has its own batch fluid dispenser to dispense reagents onto the batch of slides. In on embodiment, the group fluid dispenser dispense antibodies, probes, detection reagents to all slides depending on the protocol defined for each slide, and the batch dispensers dispense bulk reagent to each batch, thus freeing the group fluid dispense from dispensing bulk reagents to all slides.

12 Claims, 4 Drawing Sheets

(56) References Cited

U.S. PATENT DOCUMENTS 7,744,817 B2 * 6/2010 Bui .............................. 422/68.1
2002/0072122 A1 * 6/2002 Copeland et al. ............... 436/46
2007/0053798 A1 3/2007 Johnson et al.

* cited by examiner

STAINING INSTRUMENTS AND METHODS

This application is a National Stage Application of PCT/AU2009/000771, filed 16 Jun. 2009, which claims benefit of Serial No. 2008903057, filed 16 Jun. 2008 in Australia and U.S. Ser. No. 61/061,767, filed 16 Jun. 2008 and which applications are incorporated herein by reference. To the extent appropriate, a claim of priority is made to each of the above disclosed applications.

FIELD

The present invention relates to improved apparatus and methods for staining tissue mounted on microscope slides.

BACKGROUND

A number of techniques have been developed that involve placing a biological sample onto a substrate. Examples of these techniques include placing tissue samples from biopsies onto microscope slides, and micro-array analysis of samples. In histology, biological samples are attached to a microscope slide and stained to enhance the visibility of features of the tissue. Examples include routine staining, using haematoxylin and eosin stains to improve visibility of cell walls and the cell nucleus. In advanced staining, antibodies are applied to the tissue and then stained to identify the presence or absence of particular proteins, which may be indicative of disease. Other reagents may be applied to tissue such as RNA/DNA probes, which, during a sequence of reactions on the tissue, may bind to DNA in the cell nucleus. The hybridised DNA may then be stained to identify presence or absence of DNA of interest.

The number of proteins that may be used in investigation, research or diagnosis is large, and ever increasing. Similarly, the number of genes of interest is also increasing. If an automated instrument is to apply the wide range of reagents used in diagnosis or research, then the instrument must have flexibility. However, it is also important that samples are completed quickly and efficiently.

One instrument that is used to test slides is the Bond-max automated advanced staining instrument sold by Leica Microsystems, and described in application number WO 04/001390A1: BIOLOGICAL REACTION APPARATUS WITH DRAINING MECHANISM. A robotic arm is used to dispense reagent onto the slides located onto the instrument. The slides are loaded into the instrument in batches, which provides flexibility, as the instrument can start processing a first batch before a second batch is loaded. The capacity of the instrument, and its ability to process multiple batches simultaneously, is limited by the number of batches, the protocols and processing time of each slide, and the speed of the robotic arm in completing its tasks. There is a need to increase the flexibility of automated staining instruments, such as by decreasing processing time for slides, including batches of slides.

SUMMARY

In one aspect, there is provided an instrument for applying reagents to a group of microscope slides, having: a plurality of slide supports; a first set of one or more reagent containers; a second set of one or more reagent containers; a group fluid dispenser for dispensing fluid drawn from one or more reagent containers of the first set of reagent containers, and a batch fluid dispenser for dispensing fluid drawn from one or more reagent containers of the second set of reagent containers.

In one form the slides are grouped into a plurality of batches.

In one form the group fluid dispenser is mounted on a robotic arm to dispense reagent to all the slides.

In one form the batch fluid dispenser is mounted to a robotic arm to dispense fluid onto one of the batches of slides.

In another aspect, there is provided an apparatus for dispensing fluid onto a plurality of substrates, comprising: a group of substrates, formed from one or more sub-groups of substrates; a group dispenser adapted to dispense fluid onto the entire group of substrates; and one or more additional sub-group fluid dispensers adapted to dispense fluid onto one or more sub-groups of substrates.

Preferably, each of the one or more sub-group fluid dispensers is located adjacent to the one or more sub-groups of substrates upon which it is to dispense fluid.

In another aspect, there is provided a method of dispensing reagent onto a group of slides comprising the steps of applying reagent from a group fluid dispenser to slides in the group of slides; and applying reagent from a plurality of batch fluid dispensers to a corresponding plurality of batches of slides, where the group of slides consists of two or more batches of slides.

DETAILED DESCRIPTION

The apparatus 10 shares many common elements and operational methods with the Bond-max instrument sold by the applicant, and in part described in international patent application No. WO 04/001390A1, titled BIOLOGICAL REACTION APPARATUS WITH DRAINING MECHANISM, which is hereby incorporated by reference. Also incorporated by reference is the Bond-max user manual, which also describes the operation of the Bond-max instrument. If there is a conflict between the aforementioned documents, the user manual should be read as the correct description.

Figure 1:
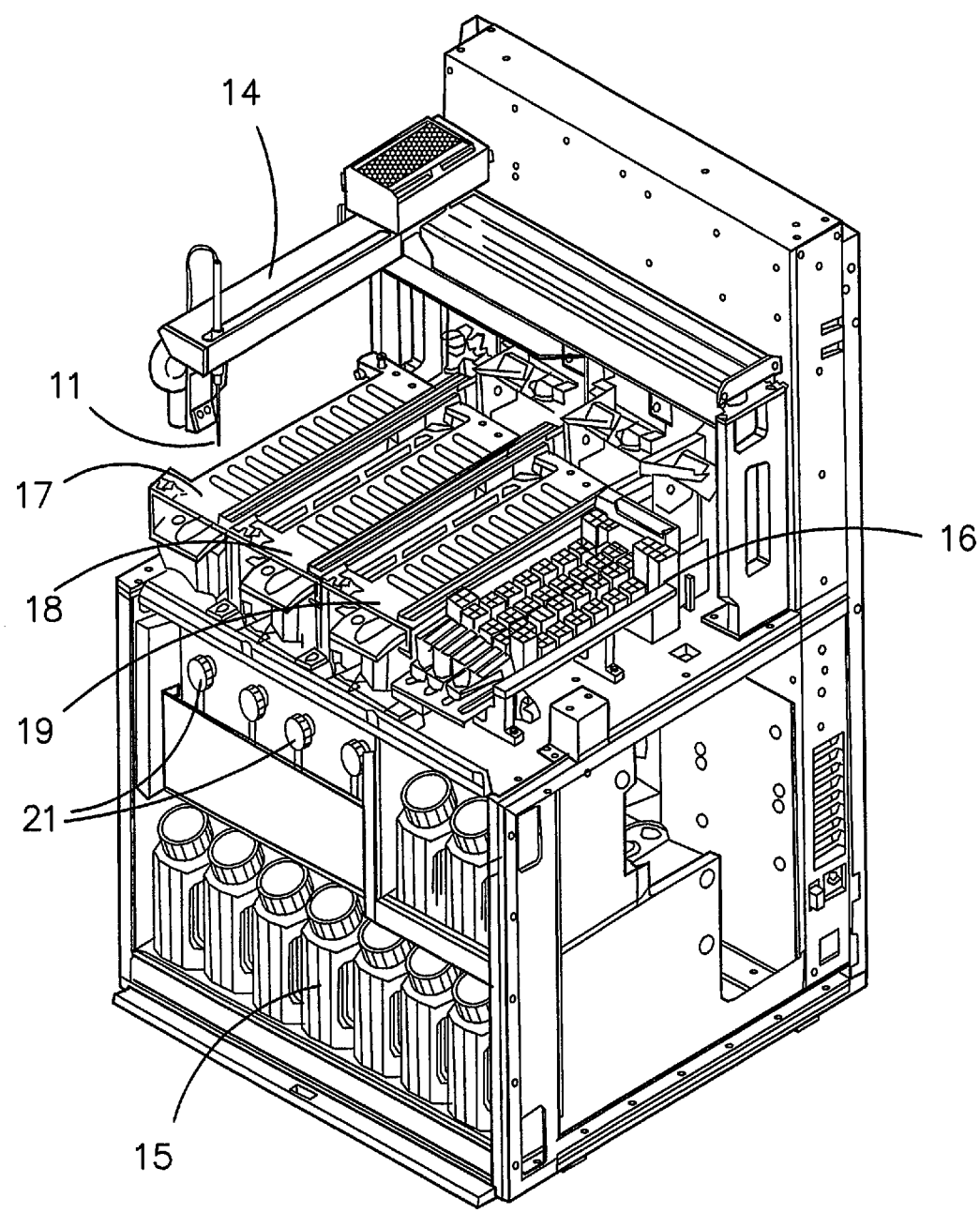
FIG. 1 is a schematic drawing of an apparatus having multiple fluid dispensers.

The apparatus 10 shown in FIG. 1 is a slide-staining instrument used to stain tissue mounted to microscope slides, but may also be used to apply fluids to substrates, such as micro array plates or other substrates used for biological testing. The apparatus 10 includes a group fluid dispenser 11 mounted to a robot arm 14, a first set of reagents, in containers 15, a second set of reagents 16, and slide staining assemblies 17, 18 and 19. Also shown are syringe pumps 21, in fluid connection with reagent containers 15.

The apparatus 10 is operated by a computer (not shown) used to instruct the apparatus of the protocols to be applied to each slide. A computer internal to the apparatus 10 receives information on the protocols to be applied to the slides, and controls the various functions of the apparatus 10, including operation of the robotic arm 14, slide staining assembly 17, 18 and 19, and reagent dispensation. In relation to systems not connected to the operation or function of the batch and group fluid dispensers, such as slide loading, slide identification, protocol identification, slide heating, and covertile opening and closing, the apparatus 10 operates in the same way, and uses the same or similar components, to a Bond-max instrument as sold by the applicant. Where a feature of a fully functioning instrument is not described in the present application, it can be taken that the feature would operate as per a standard Bond-max instrument sold by the applicant and described in the documents incorporated by reference herein.

Figure 2:
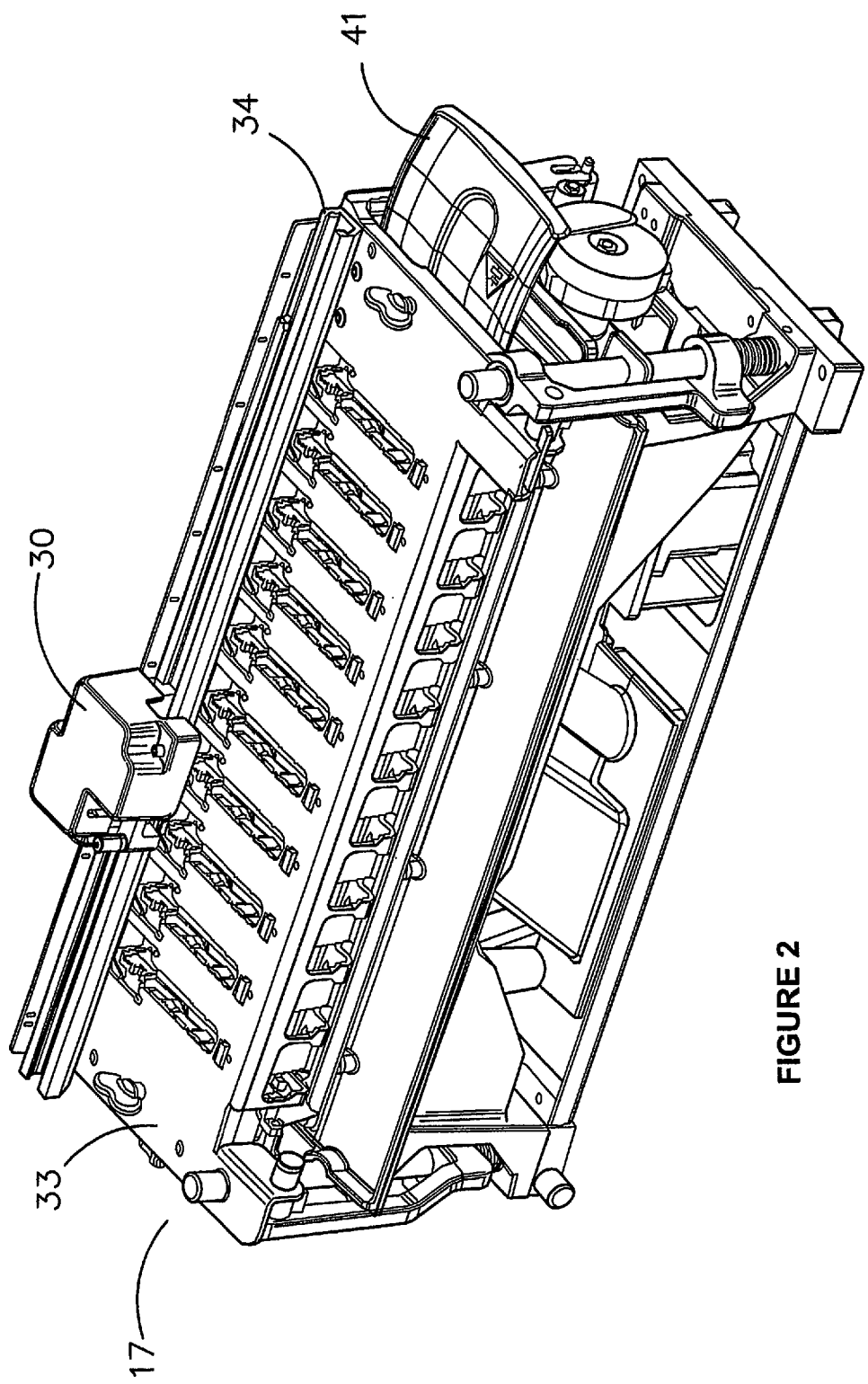
FIG. 2 is a schematic drawing of a portion of the apparatus of FIG. 1 showing a slide staining assembly and a fluid dispenser.
Figure 3:
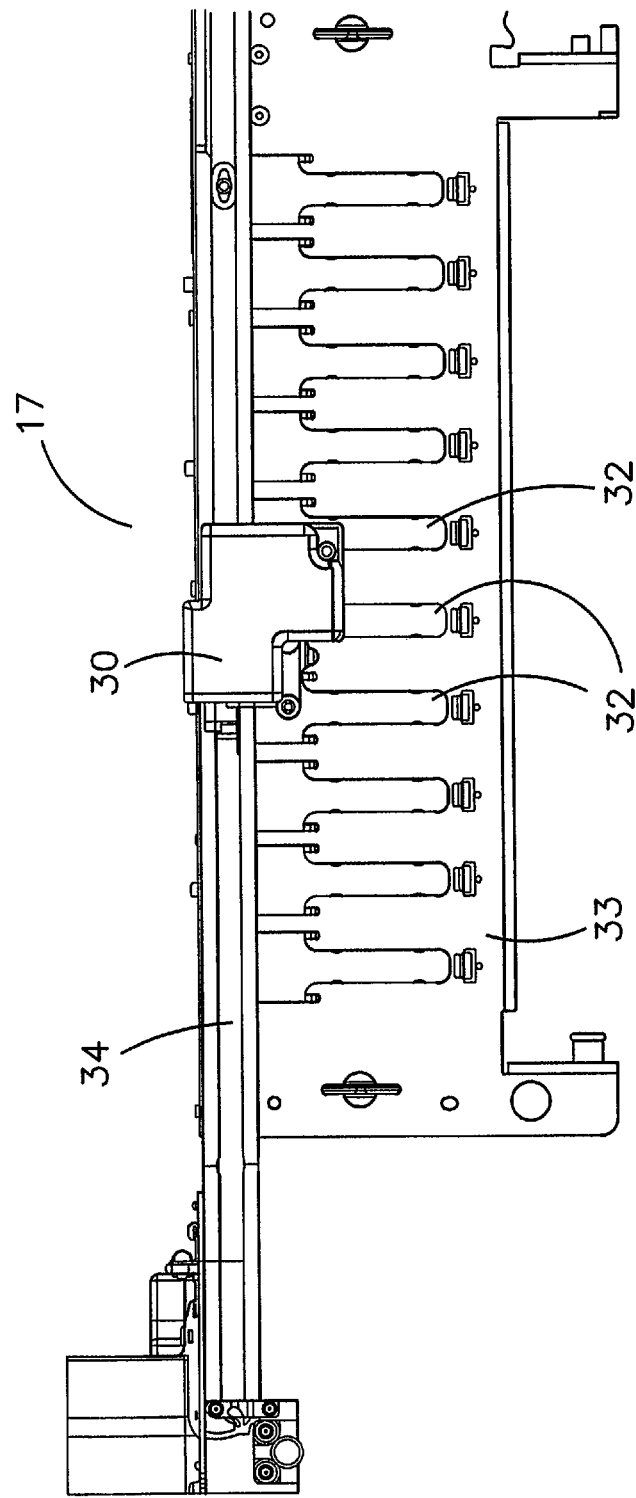
FIG. 3 is a schematic drawing of a fluid dispenser and slide staining assembly of the apparatus of FIG. 1.

Each slide staining assembly 17, 18 and 19 has a corresponding batch fluid dispenser 30, as shown in FIGS. 2 and 3.

In FIGS. 2 and 3, the slide staining assembly 17 (which in this embodiment is identical to the other slide staining assemblies 18 and 19) is shown, having ten slide supports 32 under a cover 33. In operation a batch of slides is loaded into one of the slide staining assemblies 17, 18 and 19 on a Bond slide tray 41. The slides in the tray 41 are located to correspond with the location of the slide supports 32, and therefore in operation, a slide may be located on each slide support 32. Each slide support 32 includes a heater element, for heating the slide and tissue, and has a locating mechanism for moving a covertile on each slide in the same way as Bond-max instruments operating at the time of filing this application.

Figure 4:
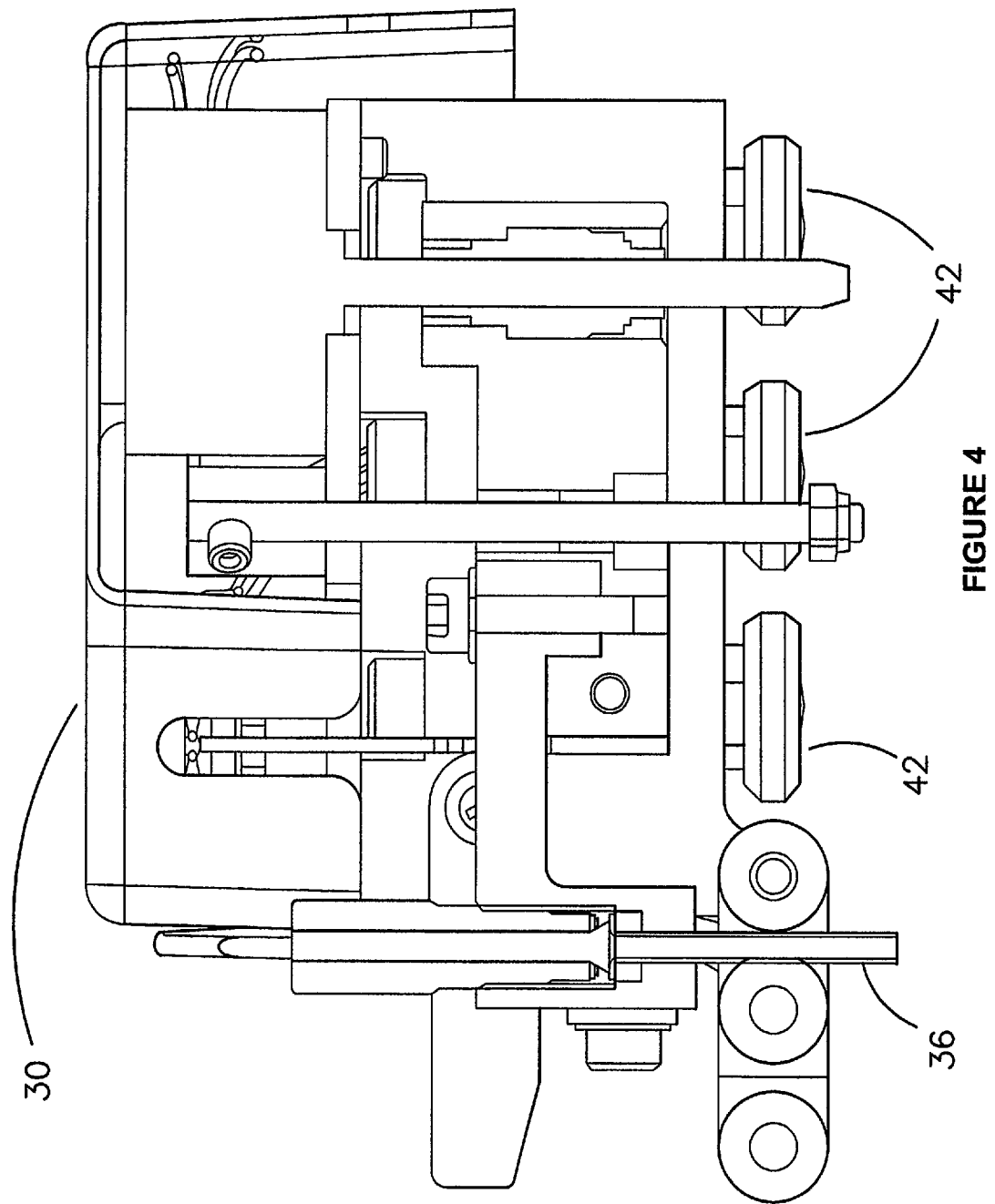
FIG. 4 is a schematic drawing of a cross section of a fluid dispenser head of the fluid dispenser shown in FIGS. 2 and 3.

The slide staining assembly 17 is located adjacent to a batch fluid dispenser 30 as shown in FIGS. 2 and 3. The batch fluid dispenser 30 includes a rail 34 along the side of the slide staining assembly 17, and a dispense head 36 (FIG. 4) adapted to move along the rail 34 so that fluid is able to be dispensed on each of the slides in the assembly 17. An energy chain device is used to drive the dispense head 36 along the length of the rail 34 to the slide required. In one example, the dispense head 36 is moved along the rail 34 from one end to the other, stopping at a position adjacent each slide, and dispensing reagent onto the slide to interact with the tissue mounted thereon. The energy chain houses a flexible fluid conduit, which terminates in the dispense head 36, to direct fluid onto the slide. The conduit is attached to a syringe pump 21 dedicated to the specific dispenser. Thus in the instrument shown, each of the three batch fluid dispensers 30 has its own syringe pump 21. Fluid may be drawn from a number of reagent containers 15. In the present example each of the aforementioned reagent containers 15 has its own manifold. Each manifold is connected to all the syringe pumps 21 via individual conduits. Each syringe pump 21 has a selectable valve structure that allows the syringe pump 21 to fluidly connect to the desired manifold, and thus access the desired fluid type. For example, if dispenser 30 was required to dispense alcohol, the valve would move to open the connection to the conduit from the alcohol reagent container, and the syringe pump 21 would draw alcohol through the conduit into the syringe until the desired volume was attained. The syringe pump 21 then closes the valve to the alcohol container, and opens the connection to the batch fluid dispenser 30. The syringe pump 21 then pushes the desired volume of fluid along the conduit to the batch fluid dispenser 30, where alcohol is dispensed onto the appropriate slide 32.

The amount of fluid drawn into the syringe pump 21 is determined by the volume of fluid in the conduit, as well as the number of slides requiring fluid and the volume of dispense per slide. The batch fluid dispenser 30 can therefore dispense a reagent onto one or more slides, by stopping adjacent each slide location. Once the fluid has been dispensed onto the slides, the syringe pump 21 will be empty, but fluid will be retained in the conduit. In order to flush the conduit fluid, the batch fluid dispenser 30 moves to the end of the slide staining assembly 17, 18, 19, where a washing station (not shown) is located. The washing station has an aperture to receive fluid from the batch fluid dispenser 30, whereupon the fluid received by the washing station is directed to a waste container. Typically, in the present embodiment, the syringe pump 21 will push a volume of the next fluid to be dispensed through the conduit and to waste to wash out the previous fluid. Once old fluid has been flushed, the batch fluid dispenser 30 may move to the slides again and dispense reagent as required.

In certain situations, some of the fluids are incompatible, for example, they may not be miscible. In such a situation where it is determined that the new fluid may not satisfactorily wash out the old fluid from the conduit, an intermediary fluid may be used.

An example of incompatible fluids would be distilled water and Dewax fluid. However, alcohol is miscible in both and therefore would be used as an intermediary fluid to remove one fluid before application of a new fluid.

In operation of the apparatus 10, having slides each with a tissue sample mounted thereon, each slide will have a protocol assigned to it, based on the type of reagent (antibody or probe) to be applied to the tissue sample on the slide. A typical protocol has an initial fluid dispense for each slide, application of further fluid, for example a Dewax fluid for removing wax from a sample, application of Epitope retrieval fluid, application of specific reagent for that sample, various detection fluids (stains), all or some of which may be interspersed with the application of wash fluid to remove the previous fluid.

Application of the fluids may in some cases need to be done at specific intervals, for example antibodies may need to be left on a sample for a specific amount of time, before being washed off. Staining of tissue can be affected if fluid is left on for too long, or if fluid levels are not replenished causing tissue to dry out. There are also times when no fluid should be dispensed onto a slide, for example incubation time, and therefore the robotic arm and dispenser may remain idle for a period of time before the next operation is required. Thus timing of the dispensation of fluid can be critical, which can cause scheduling issues when running two or more batches simultaneously.

It is not necessary to load all three trays at once. It is possible to load a first tray having between one and ten slides, into a staining assembly 17, 18, 19, and start the operation of the instrument. At any time, other trays may be loaded, which is defined as batch processing. That is, the apparatus 10 deals with each tray of slides as batches, and can begin operations on a newly entered batch before completing operations on a previously loaded batch. In the Bond-max instrument as in the apparatus 10, there are three slide staining assemblies 17, 18 and 19 that represent three batches when loaded, however in the Bond-max instrument there is only one dispenser capable of dispensing fluid onto all slides in the slide staining assemblies. Thus in the Bond-max instrument, one robot must undertake all fluid dispensing tasks on all batches of slides. In apparatus 10, as described below, the operation of the group fluid dispenser 11 has been reduced by the use of specific batch fluid dispensers 30 plumbed into reagent containers 15.

In operation, the fluid dispenser 11 on robotic arm 14 moves along the line of slides in a batch within a slide staining assembly 17; 18, 19 and undertakes the required dispensation of fluid on all slides in the batch before moving to another slide assembly 17, 18, 19.

In the apparatus 10, reagent containers 16 may contain reagents such as detection reagents (conjugating reagents and stains), antibodies and probes. Given their small volumes and high value, these containers are not plumbed into any dispenser, as the fluid lines and washing would waste too much reagent. Instead, the group fluid dispenser 11 has a pipette used to withdraw reagent directly out of the required reagent container 16. In the apparatus 10 shown, over thirty different reagent containers 16 may be loaded into the apparatus 10, and these typically include one detection system consisting of nine reagents, with the remainder being various antibodies or probes. It is therefore possible to apply a different antibody to most slides. In operation, it is necessary to rinse out the group fluid dispenser 11 between dispensations of different antibodies, to prevent cross contamination. Therefore the robot arm 14 may need to move from one of the reagent containers 16 to draw fluid, then to a slide to dispense fluid, then to a wash station to wash the dispenser pipette, then to another reagent container 16, then to a new slide. Thus the robot arm may be in use for a considerable period of time to dispense fluid onto ten slides in a single batch. During this period, dispensation of other fluids onto other batches cannot take place from the robot arm 14 and dispenser 11, as the group fluid dispenser is fully utilised. In the apparatus 10, batch fluid dispensers 30 as shown in FIG. 2 are used to dispense reagents from reagent containers 15 onto the slides. For example, while group fluid dispenser 11 is dispensing antibodies onto the slides in slide staining assembly 17, one of the batch fluid dispensers 30 may dispense reagent onto the slides in another batch, or slide staining assembly 18 and/or 19.

Thus in operation, the group fluid dispenser 11 can dispense reagent onto each slide in a batch, while the dispensers 30 associated with each slide staining assembly 17, 18 and 19 can move from side to side in their own batch and dispense reagent. This may be done simultaneously as required, thus freeing the group fluid dispenser 11 and robot arm, and allowing the batches to be completed more quickly. The group fluid dispenser 11 now has fewer dispenses to make, providing greater free time between dispenses. This makes scheduling a new batch much easier as the gap between times the group fluid dispenser (dispenser 11) is in use is larger, and the time required by the group fluid dispenser 11 to dispense some reagents may be shorter, as some dispensing may be undertaken by the batch dispensers (dispensers 30) to undertake a dispense on all sides is shorter. Thus, it is much easier to interleave the operations of the group fluid dispenser 11 in one batch into the operations of the group fluid dispenser 11 in another batch, and subsequently this reduces the time to complete three batches.

Typical reagents that the batch fluid dispenser 30 would dispense include reagents such as deionised water, alcohol, buffer fluid, Epitope retrieval fluid, and Dewax fluid. These fluids may be called bulk fluids, as they typically are stored in reagent containers 15 of between 2000-5000 ml. In contrast, the reagent containers 16 typically hold between 5-30 ml.

In the present embodiment, the batch fluid dispensers 30 use an optical sensor to detect when they are in the correct position. The batch fluid dispenser 30 is moved by a stepper motor, which is controlled to step a predetermined number of steps from one dispense position to the next. Once the motor has driven the batch fluid dispenser 30 the assigned number of steps, the system checks the optical sensor to determine whether the batch fluid dispenser 30 is in the correct position relative to the slide. If the batch fluid dispenser 30 is not in the correct position, the system moves the batch fluid dispenser 30 forward along the track 34 until it detects that it is in the correct position. While moving along track 34, the batch fluid dispenser 30 is supported in the track 34 by guide wheels 42.

The apparatus 10 may operate with one, two or three slide trays loaded into the three staining assemblies. Other examples of apparatus may not be limited to three slide staining assemblies, and for example may have two, or more depending on the throughput and size of apparatus required.

The claims defining the invention are as follows:

1. An instrument for applying reagents to a group of microscope slides arranged into a plurality of batches, the instrument comprising:
    a plurality of slide supports supporting one of the plurality of batches;
    a first set of one or more reagent containers;
    a second set of one or more reagent containers;
    a group fluid dispenser for dispensing fluid drawn from one or more reagent containers of the first set of reagent containers onto any of the microscope slides the group of microscope slides; and
    a batch fluid dispenser for dispensing fluid drawn from one or more reagent containers of the second set of reagent containers onto any of the microscope slides in a corresponding one of the batches of microscope slides,
    wherein the batch fluid dispenser is configured to dispense the fluid drawn from one or more reagent containers of the second set of reagent containers on a first slide in the corresponding batch of the plurality of batches at the same time that the group dispenser dispenses the fluid from one or more reagent containers of the first set of reagent containers on a second slide of the group of microscope slides.

2. The instrument of claim 1 wherein the group of microscope slides are divided into a plurality of batches by the plurality of slide supports.

3. The instrument of claim 1 wherein the group fluid dispenser is mounted on a first robotic arm,
    wherein the first robotic arm is configured to dispense reagent to all the slides.

4. The instrument of claim 3 wherein the batch fluid dispenser is mounted to a second robotic arm,
    wherein the second robotic arm is configured to dispense fluid onto only one of the plurality of batches of slides.

5. A method of dispensing reagent onto a group of slides comprising the steps of:
    applying a first reagent from a group fluid dispenser to any one of the slides in the group of slides, wherein the group of slides comprises a plurality of batches of slides, each batch being held in a separate slide staining assembly, each slide staining assembly comprising at least one slide support member that holds at least one slide, and a cover disposed over the at least one slide support member; and
    applying a second reagent from one of a plurality of batch fluid dispensers, each batch fluid dispenser being movable along a length of only one of the slide staining assemblies and corresponding to one of the plurality of batches and each batch fluid dispenser applying the second reagent only to slides of the batch of slides to which the batch fluid dispenser corresponds,
    wherein the first reagent is applied to one slide of the group of slides at the same time that the second reagent is applied to another slide of the batch of slides.

6. An apparatus for dispensing fluid onto a plurality of substrates forming a group of substrates, the group of substrates being made up of a plurality of batches of at least one substrate, the apparatus comprising:
    a rack configured to hold the group of substrates in the plurality of batches, the rack comprising a plurality of substrate staining assemblies, each substrate staining assembly holding one of the batches of at least one substrate and each substrate staining assembly comprising at least one substrate support member that holds the at least one substrate, and a cover disposed over the at least one substrate support member;

at least one batch dispenser moveable along a length of only a first batch of the plurality of batches of substrates, and configured to only dispense a first fluid onto a first substrate of the first batch of the plurality of batches of substrates, a group dispenser configured to dispense a second fluid onto a substrate of any of the plurality of batches; and wherein the at least one batch dispenser is configured to dispense the first fluid onto the first substrate of the first batch of the plurality of batches at the same time that the group dispenser dispenses the second fluid onto a second substrate of the plurality of the substrates.

7. The apparatus of claim 6, wherein the at least one batch dispenser is located adjacent to the first batch of substrates upon which the at least one batch is to dispense fluid.

8. The apparatus according to claim 6, wherein the rack holds the group of substrates in the first batch and a second batch, each batch comprising at least one substrate;

wherein the at least one batch dispenser comprises:
   a first batch dispenser configured to dispense fluid onto only substrates of the first batch;
   a second batch dispenser configured to dispense fluid onto only substrates of the second batch; and
wherein the first batch dispenser is configured to dispense fluid onto a substrate of the first batch at the same time that the group dispenser dispenses fluid onto a substrate of the second batch.

9. The apparatus according to claim 8, wherein the second batch dispenser is configured to dispense fluid onto a substrate of the second batch at the same time that the group dispenser dispenses fluid onto a substrate of the first batch.

10. The apparatus according to claim 8, wherein the first batch dispenser is located adjacent to the first batch of substrates.

11. The apparatus according to claim 10, wherein the second batch dispenser is located adjacent to the second batch of substrates.

12. The instrument of claim 8, wherein the group dispenser is mounted on a robotic arm to dispense reagent to all the slides.

* * * * *